United States Patent [19]

Axelgaard et al.

[11] Patent Number: 4,819,328
[45] Date of Patent: Apr. 11, 1989

[54] ELECTRICAL STIMULATION ELECTRODE MANUFACTURING METHOD

[75] Inventors: Jens Axelgaard, 730 Golden La., Fallbrook, Calif. 92028-3446; Theodore Grussing, Huntington Beach, Calif.

[73] Assignee: Jens Axelgaard, Fallbrook, Calif.

[21] Appl. No.: 114,457

[22] Filed: Oct. 28, 1987

Related U.S. Application Data

[63] Continuation-in-part of Ser. No. 745,018, Jun. 14, 1985, Pat. No. 4,722,354.

[51] Int. Cl.⁴ .............................................. A61N 1/04
[52] U.S. Cl. ...................................... 29/855; 29/877; 29/527.2; 156/289
[58] Field of Search ...................... 29/458, 527.2, 530, 29/855, 877; 128/639, 640, 641, 798, 802, 803; 156/148, 289; 428/230, 247, 256

[56] References Cited

U.S. PATENT DOCUMENTS

| | | | |
|---|---|---|---|
| 1,989,282 | 1/1935 | Kimble et al. | 128/798 |
| 4,092,985 | 6/1978 | Klufman | 128/802 X |
| 4,243,051 | 1/1981 | Witteman | 128/798 |
| 4,708,149 | 11/1987 | Axelgaard et al. | 128/798 |

Primary Examiner—Timothy V. Eley
Attorney, Agent, or Firm—Walter A. Hackler

[57] ABSTRACT

A transcutaneous nerve and/or muscle stimulation electrode manufacturing method provided which enables rapid assembly of an electrode. Stretchability is provised by a conductive fabric which includes an array of conductive fibers with interstitial areas therebetween. A conductive adhesive fills interstitial areas of the conductive fabric and provides for adhering the electrode to the patient's skin.

9 Claims, 2 Drawing Sheets

ELECTRICAL STIMULATION ELECTRODE MANUFACTURING METHOD

The present invention is a continuation-in-part of U.S. patent application Ser. No. 745,018, filed June 14, 1985, now U.S. Pat. No. 4,722,354, issued Feb. 2, 1988.

The present invention generally relates to electrodes and, more particularly, to electrodes suitable for transcutaneous nerve and/or muscle stimulation.

Continued development of electrical medical devices has produced a need for a variety of electrodes.

Although many of these electrodes have, as a design objective, good electrical signal transmission between a patient's skin surface and electrical leads interconnected with a device, each has specific requirements dependent upon the type of apparatus for which it is to be used.

As an example, electrocardiograph (EKG) and electroencephalograph (EEG) machines are primarily monitoring type devices which require small contact surfaces, or area, with the patient's skin.

On the other hand, transcutaneous electric nerve stimulation (TENS), and muscle stimulation devices require relatively large skin surface contact to effect such nerve and muscle stimulation.

Transcutaneous electrical nerve stimulation is useful, for example, in post-operative and chronic pain control, while muscle stimulation is useful, for example, in maintaining and development of muscle tissue. Electrodes suitable for use in nerve and muscle stimulation preferably provide a uniform electrical coupling across the skin electrode interface.

As hereinbefore noted, electrodes suitable for nerve and/or muscle stimulation may be relatively large having dimensions of several inches or more.

Because nerve and/or muscle stimulation causes muscle contraction, a considerable amount of skin movement is associated therewith.

Additionally, perspiration from the skin is more likely to loosen or disrupt the electrode because of its large size. As should be apparent, the larger the electrode, the longer the evaporation path, or distance, the perspiration occurring at the center regions of the electrode must travel in order to evaporate, or be released to the atmosphere.

It has been found that prior art electrodes which have been secured to the surface of a patient's skin with medical adhesive tape, or the like, have a tendency to lift off from the skin because of perspiration and movement of the patient's skin during treatment.

Because an electrode suitable for nerve and/or muscle stimulation must provide for an electrical signal to be distributed over the entire surface of the electrode, the electrode must necessarily be conductive.

Prior art electrodes have utilized a number of conductive elements, such as carbon impregnated rubber and vinyl, as well as metallic foils.

However, a useful electrode must be flexible in order to accommodate relative movement of the patient's skin therebeneath as hereinabove described.

Because nerve and muscle stimulation electrodes may be utilized over a long period of time, as may be necessary in connection with sports injuries, the electrode must be compatible with the skin and flex therewith.

Insufficient flexing of the electrode can result in severe irritation of the patient's skin and electrical "hot spots" due to uneven electrode-skin contact, which manifests itself in rash and a burning sensation.

The sensation of burning may be sensed by the patient within a few minutes after application of electrical signals during nerve and/or muscle stimulation, while the rash conditions generally take a longer period of time to develop.

It has been found that the use of prior art electrodes in nerve and/or muscle stimulation results in a skin rash in up to 25% to 35% of the people undergoing treatment.

An additional problem associated with the necessary stretchability of electrodes utilized in nerve and/or muscle stimulation procedures is that while the electrode must be able to flex, or stretch, in order to accommodate skin movement during treatment, the conductivity of the electrode should not be interrupted, or distorted, due to the stretching of the electrode. The contact between the flexible portions of the electrode and electrical lead wires coupling the electrode to stimulation is particularly prone to separation and concomitant loss of electrical continuity.

Prior art electrodes have compromised the flexibility of the electrode in an effort to provide uniform current densities over the entire contact area of the electrode. These electrodes typically utilize a metallic mesh, or foil, to provide contactivity of the electrode and utilize a conductive gel between the electrode and the patient's skin in order to accommodate movement therebetween.

There is, however, relative movement between the relatively rigid electrode and the skin, which is accommodated for by the gel. This relative movement oftentimes causes the gel to move from beneath the conductive portion of the electrode, thereby limiting the useful life of the electrode on the skin.

In addition, this relative motion between the skin and the electrode does not provide for the maintenance of the position of the electrode relative to the nerve and/or muscle being stimulated.

Precision positioning of the electrode is, of course, performed by a physician, or the like, knowledgeable in the treatment method. Inaccurate placement of the electrode, or slipping of the electrode from its intended position, may significantly reduce the beneficial effects of the treatment.

Another important consideration regarding the usefulness of electrical stimulation electrode is the economy of this production. That is, because the electrodes are for personal use, they are preferably disposable. Hence, cost consideration plays an important role in the commercial success of the electrode. In this regard, the method of manufacture significantly affects the cost of the electrode.

Hence, there is a need for an inexpensive flexible electrode for use with electrical stimulation devices which adheres well to the patient's skin, is easily removed therefrom, and is able to move with the patient's skin in order to ensure proper continuous placement of the electrode relative to nerve or muscle tissue being stimulated, as well as providing long-term continuous electrical connection therewith without irritation of the skin or discomfort to the patient under treatment. The electrode and method of the present invention fulfills these needs.

SUMMARY OF THE INVENTION

A flexible transcutaneous electrical nerve and/or muscle stimulation electrode in accordance with the present invention includes an electrical conductive fabric having an array of conductive fibers with interstitial areas therebetween.

Flexible conductive adhesive means are provided and disposed on a face side of the conductive fabric for adhering the flexible transcutaneous electrical nerve and/or muscle stimulation electrode to the skin of the patient, in the interstitial areas for providing conductivity between fibers and flush with a back side of the conductive fabric for adhering an electrical lead wire to the conductive fabric, and providing an electrical conducting contact therebetween.

Interconnection with an electrical stimulation device is provided by means of an electrical lead wire, pressed against the conductive fiber.

A non-conductive sheet is disposed on the back side of the conductive fabric for preventing undesired electrical contact therewith.

Conductivity of the conductive fabric is provided by the conductive fiber which may include a blend of stainless steel and polyester, with the stainless comprising about 20 percent by weight of the resultant fiber and the polyester comprising about 80 percent by weight of the conductive fiber.

The non-conductive sheet may be any suitable stretchable plastic, which is held against the conductive fabric by means of a pressure sensitive adhesive.

The non-conductive sheet and the pressure sensitive adhesive are also operative for holding the electrical wire lead against the conductive fabric to provide electrical contact therebetween. This contact is enhanced by utilizing a stranded electrical lead wire, which may be stainless steel, and fraying an end portion thereof to thereby provide greater contact area between the electrical lead and the conductive fabric.

The electrical stimulation electrode manufacturing method in accordance with the present invention includes the steps of:

disposing a release layer on a portion of a back side of a conductive fabric;

adhering a non-conductive backing sheet onto the release layer and portions of the conductive fabric back side not covered by the release layer;

applying a conductive adhesive onto a face sheet;

disposing a face side of conductive fabric onto the conductive adhesive;

cutting the backing sheet, release layer, conductive fabric, conductive adhesive and face sheet into a plurality of individual electrodes, each electrode having a portion of the fabric back side covered by the release layer;

peeling the release layer from the fabric back side;

disposing an electrical lead wire onto the fabric back side from which the release layer was peeled;

separating the release layer from the non-conductive backing sheet;

adhering the non-conductive backing sheet over electrical lead wire and the fabric back side from which the release layer was peeled; and pressing each individual electrode to enhance adhesion of the non-conductive backing sheet to the fabric back side.

More particularly, face sheet may be continuous and the steps of disposing a release layer on a portion of the fabric back side includes disposing a plurality of strips of release layer on a portion of a tacky fabric back side.

The cutting step may form electrodes with the release layer flush with a portion of a periphery of each electrode and the step of disposing an electrical lead wire onto the fabric back includes fanning stranded portions of the electrical lead wire and pressing the fanned portion against the fabric tacky back, said fanned portion being held in a fanned configuration by the conductive adhesive flush with the fabric back side.

DESCRIPTION OF THE DRAWINGS

The advantages, and features of the present invention will be better understood by the following description and drawings in which.

DETAILED DESCRIPTION

Figure 1:
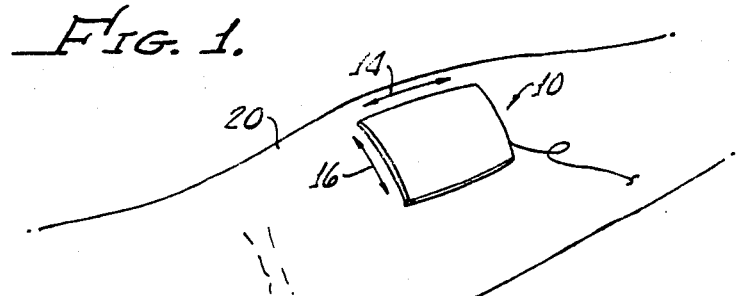
FIG. 1 is a perspective view of a flexible transcutaneous electrical nerve and/or muscle stimulation electrode in accordance with the present invention showing its disposition on a patient's skin.
Figure 2:
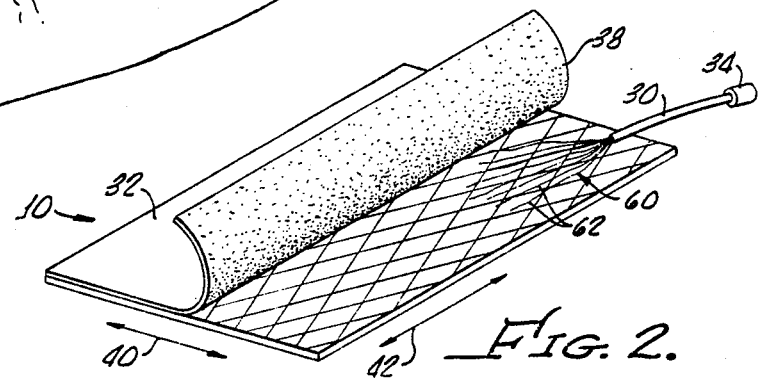
FIG. 2 is a perspective view of the stimulation electrode with a portion of a non-conductive sheet thereof peeled back to show an electrical lead wire therein.

Turning now to FIGS. 1 and 2, there is shown, in perspective view, a flexible transcutaneous electrical nerve and/or muscle stimulation electrode 10 in accordance with the present invention.

Figure 3:
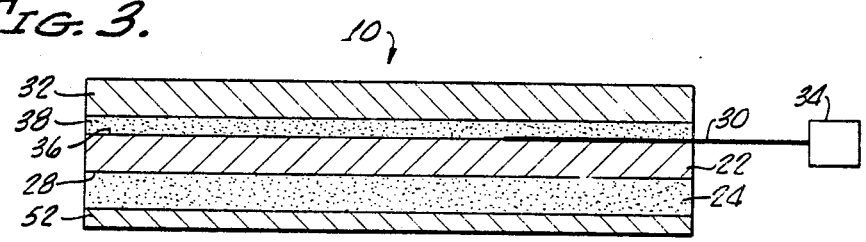
FIG. 3 is a cross-sectional view of the transcutaneous electrical nerve and/or muscle stimulation electrode generally showing conductive fabric, a flexible conductive adhesive, electrical lead wire, non-conductive sheet and a pressure sensitive adhesive.

As shown in FIG. 1 and hereinafter described in greater detail, the electrode 10 may be flexible in two directions, as indicated by arrows 14, 16, while in place on a patient's limb 20, or body, not shown. As more clearly shown in FIG. 3, the electrode 10 includes a stretchable conductive fabric 22, flexible conductive adhesive 24, which is disposed on a face side 28 of the conductive fabric 22 for adhering the flexible transcutaneous electrical nerve and/or muscle stimulation electrode 10 to the skin of a patient (not shown in FIG. 3) and electrical lead wire 30 interconnected with the conductive fabric 22 as hereinafter described, for providing electrical signals to the conductive fabric 22 when interconnected with an electrical stimulation device, not shown, by means of a connector 34, or the like. As hereinafter discussed in greater detail, it is important in the method of manufacture of the electrode 10, in accordance with the present invention, that the conductive adhesive permeate the conductive fabric 22 so that it is flush with a back side 36 in order to adhere to the electrical lead wire thereto.

In addition, a non-conductive sheet, such as a clear flexible plastic 32, disposed on the back side 36 of the conductive fabric 22 by means of a pressure sensitive adhesive 38, provides means for preventing undesired electrical contact with the conductive fabric 22, as may occur during wearing of the device.

It is important that the conductive adhesive is flush with the back side as conductive adhesive covering the opposite side 36 may cause poor adhesion of the flexible plastic thereto by the pressure sensitive adhesive 38.

It should be appreciated that the conductive fabric 22 must be isolated from outside objects and other areas of the patient's skin in order to preferentially couple electrical signals into the patient's body where prescribed by an attending physician.

Figure 4:
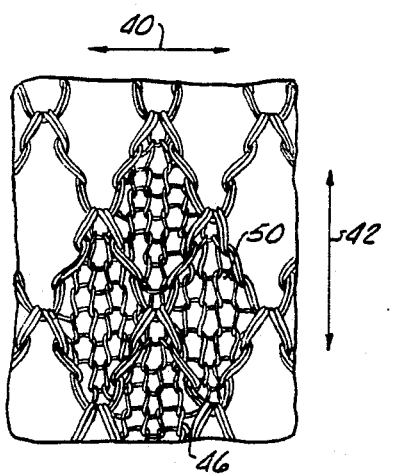
FIG. 4 is an enlarged view of the conductive fabric utilized in the present invention generally showing a honeycomb latch needle knit.
Figure 5:
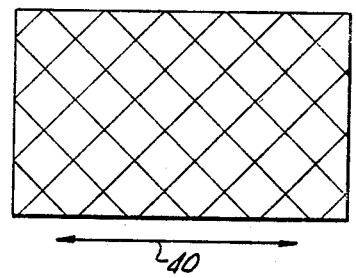
FIG. 5 is an illustration of the conductive fabric utilized in the present invention stretched in a transverse direction.
Figure 6:
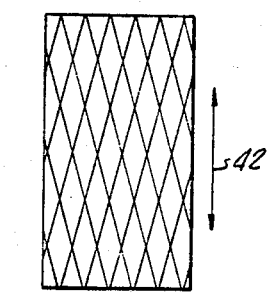
FIG. 6 is an illustration of the conductive fabric utilized in the present invention stretched in a longitudinal direction.

While woven fabrics are suitable in the present invention, it has been found that a knit fabric, preferably a one-fourth-inch honeycomb latch needle knit fabric, as depicted in FIG. 4, provides for a fabric which may be stretched up to about 100 percent greater than a first original conductive fiber dimension in the direction of stretch, see arrow 40 and FIG. 5, and up to about 20 percent greater than a second original fabric dimension in a second direction of stretch, see arrow 42 and FIG. 6, without loss of conductivity of the fabric. Knits of this nature are commercially available from knitters, such as, for example, Paragon West Knitting Mill in Anaheim Hills, Calif.

The conductivity of the fabric is provided by the individual conductive fibers 46. It has been found that a conductive fiber No. BK 50/2 manufactured by Bakaert of Belgium, which includes a blend of 20 percent 316 stainless steel and 80 percent of polyester when latch needle honeycomb knitted to a density of about 2.5 pounds per square yard, produces a conductive double-stretch knit which is particularly suitable for transcutaneous nerve and/or muscle stimulation electrodes.

The double-stretch nature of this fabric, when incorporated into the electrode of the present invention, as hereindescribed, provides for an electrode which is contourable to the shape of a patient's body or limb.

This is particularly important with relatively large stimulation/electrodes in accordance with the present invention. The electrode 10 may have dimensions in the range of, for example, 2 inches by 3 inches; hence, the electrode must be "fitted" by stretching of the electrode 10 to the skin 20 of a patient in order to provide a uniform contact therebetween.

It is particularly important that the electrode 10 and, of course, the conductive fabric 22, do not degrade during constant and repetitious movement and stretching thereof, as the electrical signals activate muscles and nerves within the patient's body which result in continued movement, or contraction, of the skin. Because the conductive fabric is a loose knit, stretching thereof does not deteriorate any of the conductive fibers therein to any substantial degree, thus causing loss of conductivity of the electrode.

In order to be effective in transmitting electrical signals to he patient's skin 20, the electrode 10 may utilize a conductive adhesive 24, such as one manufactured by Valley Lab, Inc., of Boulder, Colo., under the name Polyhesive, or other suitable adhesive.

In the manufacture of the electrode 10, the conductive adhesive 24 is poured onto the surface 28 in a liquid form, whereupon it fills the interstitial areas 50 of the conductive fabric 22.

Thereafter, the adhesive is set into a gel-like material, which has good adhesion to the patient's skin, and is releasable therefrom without the annoyance of hair-pulling and the like. The conductive adhesive 24 is commercially available from Valley Labs, Boulder, Colo., and is compatible with the skin in that it produces no irritation thereof. Alternatively, a gel-like solid conductive adhesive may be laminated to one side of the conductive fabric as will be hereinafter described. Suitable laminates are available from Promeon of Minneapolis, Minn.

Because the conductive adhesive 24 is in itself flexible, it stretches with the conductive fabric between the interstitial areas 50 defined by the fibers 46.

Turning to FIGS. 7a-f, there is shown stepwise manufacture of individual electrodes 10 in accordance with the present invention. The conductive adhesive 24 may be disposed on a face sheet, or release layer, 52, in a continuous fashion. Alternatively, the conductive adhesive, in liquid form, may be poured onto the conductive fabric 22 and allowed to permeate the conductive fabric until it is flush with the back side 36. Thereafter, it is cured into a gel and the face sheet 52 applied thereto. It should also be appreciated that the conductive adhesive may be in a gel form before application to the conductive fabric 22 in which case it is laminated, or pressed, into the fabric. Typically, the thickness of the conductive adhesive on the surface 28 is between about 0.5 mm to about 3 mm, preferably 1 mm, while conductive adhesive on the opposite side 36 is flush therewith.

Before application of the conductive adhesive 24 onto the conductive fabric, one or more release layer strips 56 are disposed on the opposite side 36 (see FIG. 3) over which the non-conductive plastic 32 is adhered with a pressure-sensitive adhesive 38. It is preferred that the non-conductive backing sheet be formed of a clear material in order that the weave or knit of the conductive fabric can be observed as well as with the electrical lead 30 and its contact with the conductive fabric.

Figure 7A:
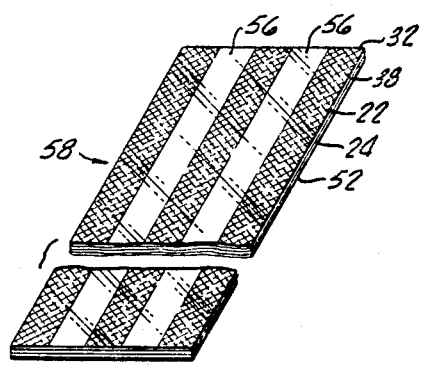
FIGS. 7a–7f are perspective type drawings showing the steps of manufacture of electrodes manufactured in accordance with the present invention.
Figure 7B:
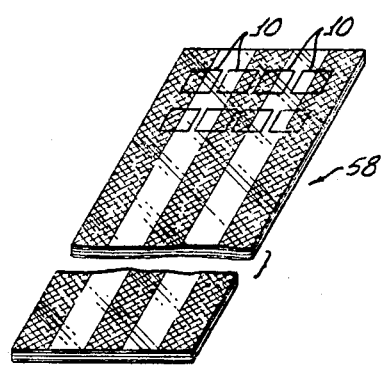

Thereafter, as shown in FIG. 7b, a die, not shown, is used to cut individual electrode 10 from the continuous layered structure 58, with each electrode 10 having a portion of the fabric back side 36 covered by the release layer 56.

Figure 7C:
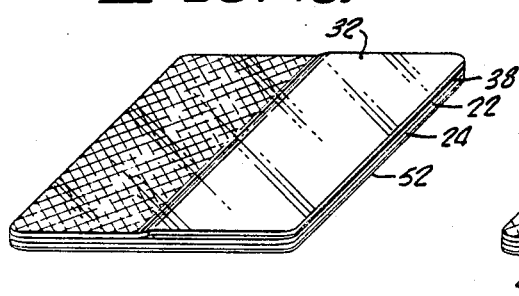
Figure 7D:
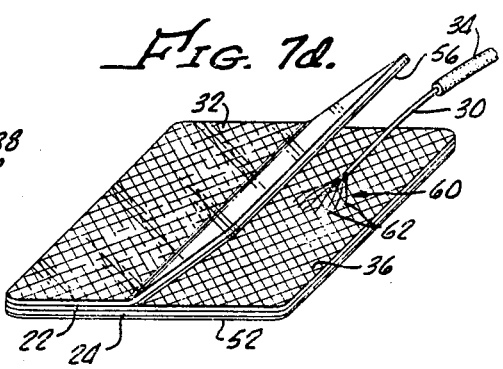

Thereafter, as shown in FIG. 7c and d, the release layer is peeled from the back side 36 and an electrical lead is applied to the back side 36. In order to enhance contact therebetween, the conductive lead, which may be formed of stranded stainless steel, has an end portion 60 which is frayed and slightly spread apart. It should be appreciated that because the strands are very fine and should be maintained in a spread-apart configuration as shown in FIG. 7d, the back side 36, with conductive adhesive flush therewith is effective in holding the stranded fibers 62 in a spread-apart configuration before being permanently held in position by the pressure-sensitive adhesive 38 and backing sheet 32. It has been discovered that if too much conductive adhesive bleeds through the conductive fabric and covers the back side 36, good adhesion to the backing sheet 32 may not occur.

Figure 7E:
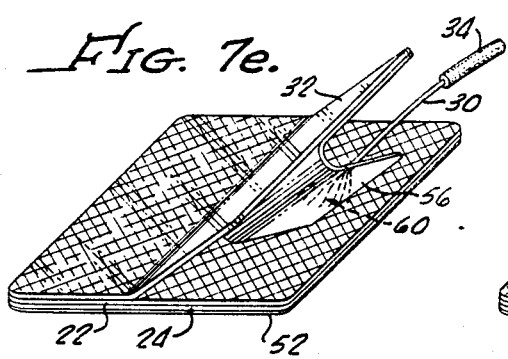
Figure 7F:
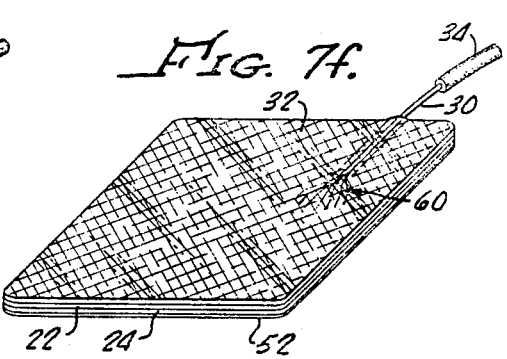

While the frayed end 60 is held against the conductive fabric 22, the release layer 56 is peeled from the backing sheet 32 as shown in FIG. 7e and removed. Thereafter, the backing sheet is laid down over the frayed end 60 of the lead 30 and pressed or rolled to insure good adhesion between the backing sheet 30 and the opposite side 36 with the lead frayed end 60 therebetween to complete the electrode manufacture. In use, the face sheet, or release liner 52, is stripped from the electrode before application to a patient.

Although there has been hereinabove described a specific arrangement of a flexible transcutaneous electrical nerve and/or muscle stimulation electrode, in accordance with the invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the invention as defined in the appended claims.

We claim:

1. A method of producing electrical stimulation electrodes comprising:
   disposing a release layer on a portion of a back side of a conductive fabric;
   adhering a non-conductive backing sheet onto the release layer and portions of the conductive fabric back side not covered by the release layer;
   applying a conductive adhesive onto a face sheet;
   disposing a face side of conductive fabric onto the conductive adhesive;
   cutting the backing sheet, release layer, conductive fabric, conductive adhesive and face sheet into a plurality of individual electrodes, each electrode having a portion of the fabric back side covered by the release layer;
   peeling the release layer from the fabric back side;
   disposing an electrical lead wire onto the fabric back side from which the release layer was peeled;
   separating the release layer from the non-conductive backing sheet;
   adhering the non-conductive backing sheet over electrical lead wire and the fabric back side from which the release layer was peeled; and
   pressing each individual electrode to enhance adhesion of the non-conductive backing sheet to the fabric back side.

2. The method of claim 1 wherein the conductive adhesive is applied to a continuous face sheet.

3. The method of claim 2 wherein the step of disposing a release layer on a portion of the fabric back side comprises disposing a plurality of strips of release layer on a portion of the fabric back side.

4. The method of claim 3 wherein the cutting step forms electrodes with the release layer flush with a portion of a periphery of each electrode.

5. A method of producing electrical stimulation electrodes comprising:
   pouring a liquid conductive adhesive onto a conductive fabric and allowing the conductive adhesive to permeate the conductive fabric until it is flush with a back side of the conductive fabric;
   curing the liquid conductive adhesive into a gel;
   applying a face sheet to the conductive adhesive on a front side of the conductive fabric;
   disposing a release layer on a portion of a fabric tacky back side;
   adhering a non-conductive backing sheet onto the release layer and portions of the fabric back side not covered by the release layer;
   cutting the backing sheet, release layer, conductive fabric, conductive adhesive and face sheet into a plurality of individual electrodes, each electrode having a portion of the fabric back side covered by the release layer;
   peeling the release layer from the fabric back side;
   disposing an electrical lead wire onto the fabric back side from which the release layer was peeled, said electrical lead wire being held in position by the conductive adhesive flush with the back side;
   separating the release layer from the non-conductive backing sheet; and
   adhering the non-conductive backing sheet over electrical lead wire and the fabric back side from which the release layer was peeled.

6. The method of claim 5 wherein the conductive adhesive is applied to a continuous face sheet.

7. The method of claim 6 wherein the step of disposing a release layer on a portion of the fabric tacky back side composes disposing a plurality of strips of release layer on a portion of the fabric back side.

8. The method of claim 7 wherein the cutting step forms electrodes with the release layer abutting a portion of a periphery of each electrode.

9. The method of claim 8 wherein the step of disposing an electrical lead wire onto the fabric back includes fanning stranded portions of the electrical lead wire and pressing the fanned portion against the fabric tacky back, said fanned portion being held in a fanned configuration by the conductive adhesive flush with the fabric back side.

* * * * *